United States Patent [19]
Suzuki et al.

[11] Patent Number: 5,210,291
[45] Date of Patent: May 11, 1993

[54] METHOD FOR PRODUCING DICHLOROPHENYLTHIOGLYCOLIC ACID

[75] Inventors: Michio Suzuki; Hiroyuki Hata; Masato Yoshikawa; Toshiyuki Ohe; Hirokazu Kagano; Hiroshi Goda; Masahito Nakano; Masaki Teramoto, all of Hyogo, Japan

[73] Assignee: Sumitomo Seika Chemicals Co., Ltd., Hyogo, Japan

[21] Appl. No.: 794,906

[22] Filed: Nov. 20, 1991

[30] Foreign Application Priority Data

Nov. 28, 1990 [JP] Japan ................. 2-332338

[51] Int. Cl.$^5$ ............................................. C07C 319/12
[52] U.S. Cl. ....................................... 562/431; 560/17
[58] Field of Search ........................... 562/431; 560/17

[56] References Cited

U.S. PATENT DOCUMENTS 1,988,501  1/1935  Lubs et al. ........................ 562/431
3,440,288  4/1969  Hoffmann et al. ................. 568/68

FOREIGN PATENT DOCUMENTS 0290886  4/1988  European Pat. Off. .
3309142  9/1984  Fed. Rep. of Germany .
139806   7/1930  Switzerland .

Primary Examiner—Jose G. Dees
Assistant Examiner—Vera C. Clarke
Attorney, Agent, or Firm—Birch, Stewart, Kolasch and Birch

[57] ABSTRACT

The present invention is directed to a method for producing dichlorophenylthioglycolic acid which comprises reacting monobromodichlorobenzene or trichlorobenzene with a thioglycolate in a ratio of 0.5 to 2.5 mols of the latter to 1 mol of the former in a polar solvent, and to a method for producing dichlorophenylthioglycolic acid comprising further reacting the reaction mixture obtained as above with a monohalogenoacetate.

The method of the present invention is very useful industrially, advantageously producing dichlorophenylthioglycolic acid in high yield.

18 Claims, No Drawings

METHOD FOR PRODUCING DICHLOROPHENYLTHIOGLYCOLIC ACID

FIELD OF THE INVENTION

The present invention relates to a method for producing dichlorophenylthioglycolic acid.

Dichlorophenylthioglycolic acid is a compound which is useful as an intermediate for thioindigo pigments, chemicals for the electronic industry, pharmaceuticals and agricultural chemicals.

BACKGROUND OF THE INVENTION

The conventional methods for producing dichlorophenylthioglycolic acid are as follows:

(1) The method in which trichlorobenzene and sodium hydrosulfide are reacted at 125° C. under increased pressure in liquid ammonia solvent in the presence of copper acetate catalyst for 10 hours to yield dichlorothiophenol, which is then reacted with sodium monochloroacetate to yield dichlorophenylthioglycolic acid with a yield of 14 to 29% [Kogyo Kagaku Zasshi, 70, 1384 (1967)].

(2) The method in which dichlorobenzene is sulfonylchlorinated with chlorosulfuric acid and then reduced with a large amount of zinc powder under acidic conditions to yield dichlorothiophenol, which is then reacted with monochloroacetic acid to yield dichlorophenylthioglycolic acid with a yield of 81% (U.S. Pat. No. 3,440,288).

However, these known methods respectively have the following drawbacks.

In the method of (1) above, the use of liquid ammonia, which is difficult to handle, a difficult-to-dispose copper compound and an increased reaction pressure poses an operational problem. In addition, the yield is low.

In the method of (2) above, the process spans a long period, and a large amount of waste effluent which contains harmful heavy metals can cause environmental pollution.

As stated above, both the known methods have various problems and are not industrially advantageous. For this reason, attempts have been made to develop an industrially advantageous method for production in the relevant technical field, but there is no satisfactory method.

SUMMARY OF THE INVENTION

It is an object of the present invention to provide a method for producing dichlorophenylthioglycolic acid industrially advantageously with high yield.

Taking note of the situation described above, the present inventors conducted investigations to provide a method for producing dichlorophenylthioglycolic acid industrially advantageously with high yield under mild reaction conditions without using harmful heavy metals.

As a result, the present inventors have found that a dichlorophenylthioglycolate can be produced by reacting monobromodichlorobenzene or trichlorobenzene with a thioglycolate as shown in the following reaction scheme A.

Also, in the above-mentioned reaction, when the thioglycolate was added in excess of equivalent in order to increase the yield of a dichlorophenylthioglycolate, on the contrary the yield of the desired product dichlorophenylthioglycolate declined.

With respect to this phenomenon, the inventors conducted further investigations and found that when a thioglycolate is added in excess of equivalent, the reaction between the resulting dichlorophenylthioglycolate and the unreacted thioglycolate proceeds preferentially as shown in the reaction scheme B to yield a dichlorothiophenol salt and thus gives a mixture of dichlorophenylthioglycolate and dichlorothiophenol salt. On the other hand, when a monohalogenoacetate is added to this reaction mixture, the dichlorothiophenol salt changes easily to the dichlorophenylthioglycolate in accordance with the reaction scheme C. The inventors thus found that the yield improves in comparison with the production of a dichlorophenylthioglycolate in a single process in accordance with the reaction scheme A, and developed the present invention.

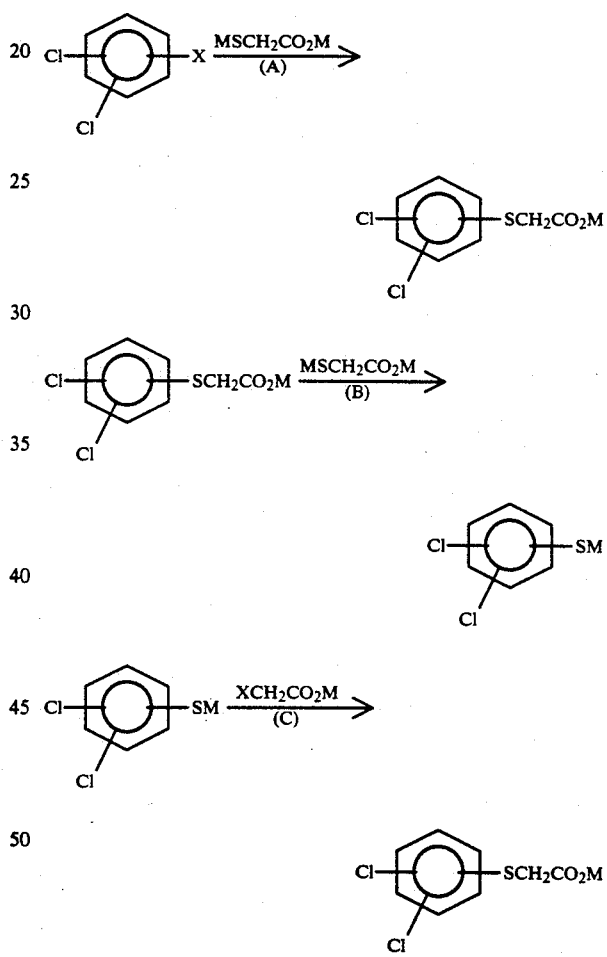

wherein X represents a chlorine atom or bromine atom; M represents an alkali metal.

Developed on the basis of these findings, the present invention relates to:

(1) a method for producing dichlorophenylthioglycolic acid which comprises reacting monobromodichlorobenzene or trichlorobenzene with a thioglycolate in a ratio of 0.5 to 2.5 mols of the latter to 1 mol of the former in a polar solvent, and (2) a method for producing dichlorophenylthioglycolic acid which comprises further reacting the reaction mixture obtained from the reaction of (1) above with a monohalogenoacetate.

DETAILED DESCRIPTION OF THE INVENTION

The monobromodichlorobenzenes which can serve as a starting material for the present invention are exemplified by 1-bromo-2,5-dichlorobenzene, 1-bromo-2,4-dichlorobenzene, 1-bromo-3,4-dichlorobenzene, 1-bromo-2,3-dichlorobenzene, 1-bromo-2,6-dichlorobenzene and 1-bromo-3,5-dichlorobenzene. The trichlorobenzenes which can serve as a starting material for the present invention are exemplified by 1,2,4-trichlorobenzene, 1,2,3-trichlorobenzene and 1,3,5-trichlorobenzene.

Reaction of monobromodichlorobenzene or trichlorobenzene with a thioglycolate is carried out normally in a polar solvent. The polar solvent used is not subject to limitation. Examples of polar solvents which can be used in the present invention include ethylene glycol, diethylene glycol, methanol, ethanol, butanol, N-methyl-2-pyrrolidone, N,N-dimethylformamide, N,N-dimethylacetamide, acetamide, formamide, caprolactam, 1,1-ethylenedipyrrolidone, tetramethylurea, hexamethylphosphoramide, acetonitrile, quinoline, pyridine, lutidine, picoline, dimethylsulfoxide, sulfolane and sulfolene, with preference given to dimethylsulfoxide, ethylene glycol, N-methyl-2-pyrrolidone, sulfolane and the like because they offer a high yield of the reaction product dichlorophenylthioglycolic acid.

The amount of solvent used is 1 to 20 times, preferably 1 to 10 times the amount by weight of the starting trichlorobenzene or monobromodichlorobenzene. Two or more of the solvents mentioned above may be used in combination.

The amount of thioglycolate used for the present invention is normally 0.5 to 2.5 times the molar amount of monobromodichlorobenzene or trichlorobenzene. Molar ratios below 0.5 result in an increase of unreacted monobromodichlorobenzene or trichlorobenzene. When the thioglycolate is used at a molar ratio exceeding about 1.0, preference is given to the method in which the side product dichlorothiophenol salt is converted to the dichlorophenylthioglycolate by the addition of a monohalogenoacetate from the viewpoint of improvement in the yield of the desired product dichlorophenylthioglycolic acid for the reason described above. However, the use of a thioglycolate in a molar ratio exceeding 2.5 is not advantageous because the increased side production of a dichlorophenylthiophenol salt necessitates the addition of a still greater amount of a monohalogenoacetate.

A usable thioglycolate is produced by reacting thioglycolic acid with an alkali metal hydroxide or alkali metal carbonate. The thioglycolate described above can also be prepared in the reaction system. The alkali metal hydroxide or alkali metal carbonate used in this case is exemplified by sodium hydroxide, potassium hydroxide, sodium carbonate, sodium hydrogen carbonate, potassium carbonate or potassium hydrogen carbonate. The amount is suitably 1.6 to 3.0 times the molar amount of thioglycolic acid.

In the present invention, the reaction temperature for the reaction of monobromodichlorobenzene or trichlorobenzene with a thioglycolate is preferably 50° to 220° C., more preferably 80° to 190° C. Temperatures below 50° C. result in too low reaction rates; temperatures above 220° C. can cause yield reductions due to side reactions. The reaction time is preferably 1 to 6 hours; reaction times longer than 6 hours can result in yield reductions due to side reactions.

When the monohalogenoacetate is added to the reaction mixture, the monohalogenoacetate can include sodium monochloroacetate, potassium monochloroacetate, sodium monobromoacetate and potassium monobromoacetate. The amount added is normally 1.0 to 4.0 times the molar amount of the resulting dichlorothiophenol salt.

The reaction temperature for the reaction of a dichlorothiophenol salt with a monohalogenoacetate is preferably 10° to 200° C., more preferably 50° to 120° C. A reaction time of 1 hour is sufficient because the rate of the reaction of a dichlorothiophenol salt and a monohalogenoacetate is high. By acidizing the resulting reaction mixture, the dichlorophenylthioglycolate can easily be converted to dichlorophenylthioglycolic acid. In the present invention, when trichlorobenzene is used to obtain a 2,5-dichlorophenylthioglycolate, the solvent is distilled off, after which the reaction mixture is heated in the presence of water and cooled for crystallization to separate the side product isomeric 2,4-dichlorophenylthioglycolate. This procedure causes crystallization of a 2,5-dichlorophenylthioglycolate alone, which is then acidized as above to yield 2,5-dichlorophenylthioglycolic acid with high purity. Examples of the acid used for the acidization include hydrochloric acid, sulfuric acid, nitric acid and phosphoric acid. The amount added is normally 1.0 to 4.0 times, preferably 1.0 to 3.0 times the molar amount of dichlorophenylthioglycolate.

In accordance with the present invention, a dichlorophenylthioglycolate or a mixture of dichlorophenylthioglycolate and dichlorothiophenol salt can be obtained by reacting monobromodichlorobenzene or trichlorobenzene with a thioglycolate under normal pressure. Also, dichlorophenylthioglycolic acid can be obtained industrially advantageously in high yield by the very simple procedure of reacting this mixture with a monohalogenoacetate.

EXAMPLES

The present invention is hereinafter described in more detail by means of the following working examples and comparative example, but the invention is not limited by these examples.

EXAMPLE 1

To a 300 ml four-necked flask equipped with a stirrer, a thermometer and a condenser were charged 24.9 g (0.110 mol) of 1-bromo-2,5-dichlorobenzene, 13.19 g (0.143 mol) of thioglycolic acid, 12.06 g (0.286 mol) of 95% sodium hydroxide and 100 g of dimethylsulfoxide, followed by stirring at 120° C. for 4 hours. Then, after distilling off the dimethylsulfoxide under reduced pressure, 100 g of water was added to the residue. After dissolving the residue therein at 100° C., the solution was cooled for crystallization and filtered to yield sodium 2,5-dichlorophenylthioglycolate, which was then dissolved in 100 g of water with heating and acidized with concentrated hydrochloric acid, filtered and dried to yield 19.6 g of a light yellowish white powder of 2,5-dichlorophenylthioglycolic acid. The yield based on 1-bromo-2,5-dichlorobenzene was 75.1%.

EXAMPLE 2

To a 300 ml four-necked flask equipped with a stirrer, a thermometer and a condenser were charged 24.9 g (0.110 mol) of 1-bromo-2,5-dichlorobenzene, 13.19 g (0.143 mol) of thioglycolic acid, 12.06 g (0.286 mol) of 95% sodium hydroxide and 100 g of dimethylsulfoxide, followed by stirring at 120° C. for 4 hours. After cooling until 100° C., 2,5-dichlorothiophenol salt produced as the side product was treated with 5.13 g (0.044 mol) of sodium monochloroacetate at the same temperature for 1 hour. Then, after distilling off the dimethylsulfoxide under reduced pressure, 100 g of water was added to 54.5 g of the residue. After dissolving the residue therein at 100° C., the solution was cooled for crystallization and filtered to yield sodium 2,5-dichlorophenylthioglycolate, which was then dissolved in 100 g of water with heating and acidized with concentrated hydrochloric acid, filtered and dried to yield 23.5 g of a light yellowish white powder of 2,5-dichlorophenylthioglycolic acid. The yield based on 1-bromo-2,5-dichlorobenzene was 90.0%.

EXAMPLE 3

15.4 g of a light yellowish white powder of 2,5-dichlorophenylthioglycolic acid was obtained in the same manner as in Example 1 except that the 1-bromo-2,5-dichlorobenzene was replaced with 20.0 g (0.110 mol) of 1,2,4-trichlorobenzene. The yield based on 1,2,4-trichlorobenzene was 59.0%.

EXAMPLE 4

19.3 g of a light yellowish white powder of 2,5-dichlorophenylthioglycolic acid was obtained in the same manner as in Example 2 except that the 1-bromo-2,5-dichlorobenzene was replaced with 20.0 g (0.110 mol) of 1,2,4-trichlorobenzene. The yield based on 1,2,4-trichlorobenzene was 74.0%.

EXAMPLES 5 through 7

2,5-dichlorophenylthioglycolic acid was obtained in the same manner as in Example 4 except that reaction temperature, molar ratio of thioglycolic acid and reaction time were changed as shown in Table 1. The results are shown in Table 1.

TABLE 1

| Ex | Halogenobenzene | Thioglycolic acid | Thioglycolic acid/Halogenobenzene (molar ratio) | Solvent | Reaction temp. Reaction time | Monohalogenoacetate | Yield of Dichlorophenyl-tioglycolic acid |
|---|---|---|---|---|---|---|---|
| 1 | Cl, Br, Cl (benzene ring) 24.9 g (0.110 mol) | 13.19 g (0.143 mol) | 1.3 | Dimethylsulfoxide 100 g | 120° C. 4 Hr. | — | 75.1% |
| 2 | Cl, Br, Cl (benzene ring) 24.9 g (0.110 mol) | 13.19 g (0.143 mol) | 1.3 | Dimethylsulfoxide 100 g | 120° C. 4 Hr. | ClCH$_2$CO$_2$Na 5.13 g (0.044 mol) | 90.0% |
| 3 | Cl, Cl, Cl (benzene ring) 20.0 g (0.110 mol) | 13.19 g (0.143 mol) | 1.3 | Dimethylsulfoxide 100 g | 120° C. 4 Hr. | — | 59.0% |
| 4 | Cl, Cl, Cl (benzene ring) 20.0 g (0.110 mol) | 13.19 g (0.143 mol) | 1.3 | Dimethylsulfoxide 100 g | 120° C. 4 Hr. | ClCH$_2$CO$_2$Na 5.13 g (0.044 mol) | 74.0% |
| 5 | Cl, Cl, Cl (benzene ring) 20.0 g (0.110 mol) | 5.06 g (0.055 mol) | 0.7 | Dimethylsulfoxide 100 g | 100° C. 6 Hr. | — | 55.7% |
| 6 | Cl, Cl, Cl (benzene ring) 20.0 g (0.110 mol) | 13.19 g (0.143 mol) | 1.3 | Dimethylsulfoxide 100 g | 140° C. 3 Hr. | ClCH$_2$CO$_2$Na 5.13 g (0.044 mol) | 72.1% |

TABLE 1-continued

| Ex | Halogenobenzene | Thioglycolic acid | Thioglycolic acid/Halogeno-benzene (molar ratio) | Solvent | Reaction temp. Reaction time | Monohalogeno-acetate | Yield of Dichlorophenyl-tioglycolic acid |
|---|---|---|---|---|---|---|---|
| 7 | Cl-C6H3(Cl)(Cl) 20.0 g (0.110 mol) | 12.15 g (0.132 mol) | 1.2 | Dimethyl-sulfoxide 100 g | 120° C. 5 Hr. | ClCH$_2$CO$_2$Na 5.13 g (0.044 mol) | 70.4% |

EXAMPLE 8

To a 500 ml flask equipped with a thermometer, a condenser and a stirrer were added 45.2 g (0.2 mol) of 1-bromo-2,5-dichlorobenzene, 23.7 g (0.4 mol) of 95% potassium hydroxide, 18.4 g (0.2 mol) of thioglycolic acid and 320 g of N-methyl-2-pyrrolidone, followed by stirring at 140° to 150° C. for 2 hours. Assay of the reaction solution by high performance liquid chromatography identified the solution as a mixture of dichlorophenylthioglycolate and dichlorothiophenol salt. Then, after distilling off the solvent, 300 g of water and 50 g of toluene were added for layer separation. To the water layer was added 45 g of concentrated hydrochloric acid, and the mixture was cooled to room temperature. The resulting crystal was filtered and dried to yield 28.7 g of 2,5-dichlorophenylthioglycolic acid. Its melting point was 129° to 131° C., and the yield was 60.5%. The results are given in Table 2.

EXAMPLE 9

Using the same procedure as in Example 8, 45.2 g (0.2 mol) of 1-bromo-2,5-dichlorobenzene, 23.7 g (0.4 mol) of 95% potassium hydroxide, 18.4 g (0.2 mol) of thioglycolic acid and 320 g of N-methyl-2-pyrrolidone were added, followed by stirring at 140° to 150° C. for 2 hours. Then, 30.4 g (0.26 mol) of sodium monochloroacetate was added to the reaction solution, followed by stirring at 90° C. for 1 hour. After distilling off the solvent, 300 g of water and 50 g of toluene were added for layer separation. To the water layer was added 45 g of concentrated hydrochloric acid, and the mixture was cooled to room temperature. The resulting crystal was filtered and dried to yield 34.0 g of 2,5-dichlorophenyl-thioglycolic acid with a yield of 71.7%. The results are given in Table 2.

EXAMPLES 10 THROUGH 13

Using the combinations of monobromodichlorobenzene or trichlorobenzene, thioglycolic acid, potassium hydroxide and solvent listed in Table 2, the reaction was carried out in the same manner as in Example 8 or 9 to yield 2,5-dichlorophenylthioglycolic acid. The results are given in Table 2.

TABLE 2

| Ex | Halogenobenzene | Thioglycolic acid | Thioglycolic acid/Halogeno-benzene (molar ratio) | Solvent | Reaction temp. Reaction time | Monohalogeno-acetate | Yield of Dichlorophenyl-tioglycolic acid |
|---|---|---|---|---|---|---|---|
| 8 | Cl-C6H3(Br)(Cl) 45.2 g (0.2 mol) | 18.4 g (0.2 mol) | 1.0 | N-methyl-2-pyrrolidone 320 g | 140~150° C. 2 Hr. | — | 60.5% |
| 9 | Cl-C6H3(Br)(Cl) 45.2 g (0.2 mol) | 18.4 g (0.2 mol) | 1.0 | N-methyl-2-pyrrolidone 320 g | 140~150° C. 2 Hr. | ClCH$_2$CO$_2$Na 30.4 g (0.26 mol) | 71.7% |
| 10 | Cl-C6H3(Br)(Cl) 45.2 g (0.2 mol) | 36.8 g (0.4 mol) | 2.0 | Ethylene Glycol 80 g | 150° C. 2 Hr. | — | 41.2% |
| 11 | Cl-C6H3(Br)(Cl) 45.2 g (0.2 mol) | 36.8 g (0.4 mol) | 2.0 | Ethylene Glycol 80 g | 150° C. 2 Hr. | ClCH$_2$CO$_2$Na 30.4 g (0.26 mol) | 73.3% |

TABLE 2-continued

| Ex | Halogenobenzene | Thioglycolic acid | Thioglycolic acid/Halogenobenzene (molar ratio) | Solvent | Reaction temp. Reaction time | Monohalogenoacetate | Yield of Dichlorophenyltioglycolic acid |
| --- | --- | --- | --- | --- | --- | --- | --- |
| 12 | trichlorobenzene 36.3 g (0.2 mol) | 25.8 g (0.28 mol) | 1.4 | Sulfolane 320 g | 160° C. 3 Hr. | — | 41.5% |
| 13 | trichlorobenzene 36.3 g (0.2 mol) | 25.8 g (0.28 mol) | 1.4 | Sulfolane 320 g | 160° C. 3 Hr. | BrCH$_2$CO$_2$Na 20.9 g (0.13 mol) | 54.5% |

COMPARATIVE EXAMPLE

In the same manner as in Example 8, 45.2 g (0.2 mol) of 1-bromo-2,5-dichlorobenzene, 23.7 g (0.4 mol) of 95% potassium hydroxide, 18.4 g (0.2 mol) of thioglycolic acid and 320 g of n-decane were added, followed by stirring at 140° to 150° C. for 10 hours. Assay of the reaction solution by high performance liquid chromatography detected no peak of 2,5-dichlorophenylthioglycolic acid or 2,5-dichlorothiophenol. Then, 200 g of water was added to the reaction solution, and the mixture was cooled to room temperature. Assay of the n-decane solution by the high performance liquid chromatography revealed that 1-bromo-2,5-dichlorobenzene remained unreacted in an amount equivalent to 98.7% of the starting material.

What is claimed is:

1. A method for producing dichlorophenylthioglycolic acid, which comprises reacting monobromodichlorobenzene or trichlorobenzene with a thioglycolate in a ratio of 0.5 to 2.5 mols of the latter to 1 mol of the former in a polar solvent at a reaction temperature of 50° to 220° C.

2. The method according to claim 1, wherein said polar solvent is dimethylsulfoxide.

3. The method according to claim 1, wherein said polar solvent is ethylene glycol.

4. The method according to claim 1, wherein said polar solvent is N-methyl-2-pyrrolidone.

5. The method according to claim 1, wherein said polar solvent is sulfolane.

6. The method according to claim 1, wherein said monobromodichlorobenzene is a member selected from the group consisting of 1-bromo-2,5-dichlorobenzene, 1-bromo-2,4-dichlorobenzene, 1-bromo-3,4-dichlorobenzene, 1-bromo-2,3-dichlorobenzene, 1-bromo-2,6-dichlorobenzene and 1-bromo-3,5-dichlorobenzene.

7. The method according to claim 1, wherein said trichlorobenzene is a member selected from the group consisting of 1,2,4-trichlorobenzene, 1,2,3-trichlorobenzene and 1,3,5-trichlorobenzene.

8. The method according to claim 1, wherein said polar solvent is at least one member selected from the group consisting of ethylene glycol, diethylene glycol, methanol, ethanol, butanol, N-methyl-2-pyrrolidone, N,N-dimethylformamide, N,N-dimethylacetamide, acetamide, formamide, caprolactam, 1,1-ethylenedipyrrolidone, tetramethylurea, hexamethylphosphoramide, acetonitrile, quinoline, pyridine, lutidine, picoline, dimethylsulfoxide, sulfolane and sulfolene.

9. The method according to claim 1, wherein the amount of said polar solvent is 1 to 20 times the amount by weight of said monobromodichlorobenzene or said trichlorobenzene.

10. The method according to claim 1, wherein the amount of said polar solvent is 1 to 10 times the amount by weight of said monobromodichlorobenzene or said trichlorobenzene.

11. The method according to claim 1, wherein said reaction temperature is 80° to 190° C.

12. The method according to claim 1, wherein the reaction time is 1 to 6 hours.

13. A method for producing dichlorophenylthioglycolic acid, which comprises further reacting the reaction mixture obtained from the reaction of claim 1 with a monohalogenoacetate at a reaction temperature of 10° to 200° C., wherein the amount of said monohalogenoacetate added is 1.0 to 4.0 times the molar amount of the dichlorothiophenol salt in said reaction mixture.

14. The method according to claim 13, wherein said monohalogenoacetate is sodium monochloroacetate.

15. The method according to claim 13, wherein said monohalogenoacetate is sodium monobromoacetate.

16. The method according to claim 13, wherein said monohalogenoacetate is a member selected from the group consisting of sodium monochloroacetate, potassium monochloroacetate, sodium monobromoacetate and potassium monobromoacetate.

17. The method according to claim 13, wherein the reaction temperature is 50° to 120° C.

18. The method according to claim 13, wherein the reaction time is 1 hour.

* * * * *